United States Patent [19]
Schultz et al.

[11] Patent Number: 6,116,237
[45] Date of Patent: *Sep. 12, 2000

[54] METHODS OF DRY POWDER INHALATION

[75] Inventors: Robert Schultz; Clyde Witham; Malcolm Hill, all of San Diego, Calif.

[73] Assignee: Dura Pharmaceuticals, Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/847,287

[22] Filed: Apr. 24, 1997

Related U.S. Application Data

[60] Provisional application No. 60/016,428, May 29, 1996.

[51] Int. Cl.$^7$ ................................................ A61M 15/00
[52] U.S. Cl. ................................ 128/203.15; 128/203.21
[58] Field of Search ...................... 128/203.12, 203.15, 128/203.23, 200.24

[56] References Cited

U.S. PATENT DOCUMENTS

| | | |
|---|---|---|
| 3,831,606 | 8/1974 | Damani . |
| 4,681,752 | 7/1987 | Melillo . |
| 4,810,488 | 3/1989 | Jinks . |
| 5,176,132 | 1/1993 | Drought et al. . |
| 5,327,883 | 7/1994 | Williams et al. . |
| 5,388,574 | 2/1995 | Ingebrethsen ........................ 128/203.26 |
| 5,469,843 | 11/1995 | Hodson . |
| 5,492,112 | 2/1996 | Mecikalski et al. . |
| 5,503,869 | 4/1996 | Van Oort . |
| 5,522,385 | 6/1996 | Lloyd et al. ......................... 128/203.26 |
| 5,524,613 | 6/1996 | Haber et al. . |
| 5,577,497 | 11/1996 | Mecikalski et al. . |
| 5,622,166 | 4/1997 | Eisele et al. . |
| 5,645,051 | 7/1997 | Schultz et al. . |
| 5,792,057 | 8/1998 | Rubsamen et al. .................. 128/203.26 |

FOREIGN PATENT DOCUMENTS

| | | |
|---|---|---|
| 248400A | 4/1992 | United Kingdom . |
| WO 90/13327 | 11/1990 | WIPO . |
| WO 94/08552 | 4/1994 | WIPO . |

OTHER PUBLICATIONS

"Inhalation Characteristics and Their Effects on In vitro Drug Delivery From DPI", Int'l Jrnl. of Pharm., 130 (1996) 231–244 from Elsevier Science.

Vidgren et al., Orion Pharmaceutica, Easyhaler—"Pulmonary Deposition of $^{99m}$TC–Labelled Salbutamol From A Novel Multiple Dose Powder Inhaler In Healthy Volunteers And In Asthmatics", J. Aerosol Med 6 (suppl), p. 72 (1993).

Vidgren et al., Orion Pharmaceutica, Easyhaler—"Single Dose Comparison Of A Metered Dose Inhaler And A Novel Multiple Dose Powder Inhaler Of Salbutamol", J. Aerosol Med. 6 (suppl), p. 79 (1993).

Moren, "Towards Satisfactory In Vitro Testing Requirments for Single And Multi–Dose Powder Inhalers", Journal of Biopharmaceutical Sciences, pp. 123–129 (1992).

Schultz et al. "Powder Aerosols With Auxiliary Means of Dispersion", Journal of Biopharmaceutical Sciences, pp. 115–121 (1992).

J.H. Bell—"Dry Powder Inhalers—Innovation, Performance Assessment and the Realities" Dec., 1992 pp. 1–17.

Information Sheets—IV. Competitive Technology—Dry Powder Inhalers Currently Marketed—Spinhaler—Fisons; Rotahaler (Glaxo); Turbuhaler (Astra); Berotec–Boehring Ingelheim; and Diskhaler (Glaxo).

D. Ganderton et al., "Dry Powder Inhalers", Advances in Pharmaceutical Sciences, pp. 165–191.

*Primary Examiner*—Aaron J. Lewis
*Attorney, Agent, or Firm*—Lyon & Lyon LLP

[57] ABSTRACT

A method for inhalation of a dry powder drug includes the steps of providing a dry powder drug composition having a drug particle size of from about 1–7 microns and a mass median aerodynamic diameter of the delivered aerosol of from about 3.5 to 5.5 microns. This composition is loaded into an inhaler which is generally flow rate independent, and with the inhaler having an inspiration flow resistance of about 0.12 to 0.21 $(cmH_2O)^{1/2}$ over the range of about 15–60 L/min. The patient inhales the drug composition from the inhaler with an inspiration flow rate of about 15–60 L/min, resulting in a delivery efficiency measured by respirable fraction greater than 20%.

12 Claims, 10 Drawing Sheets

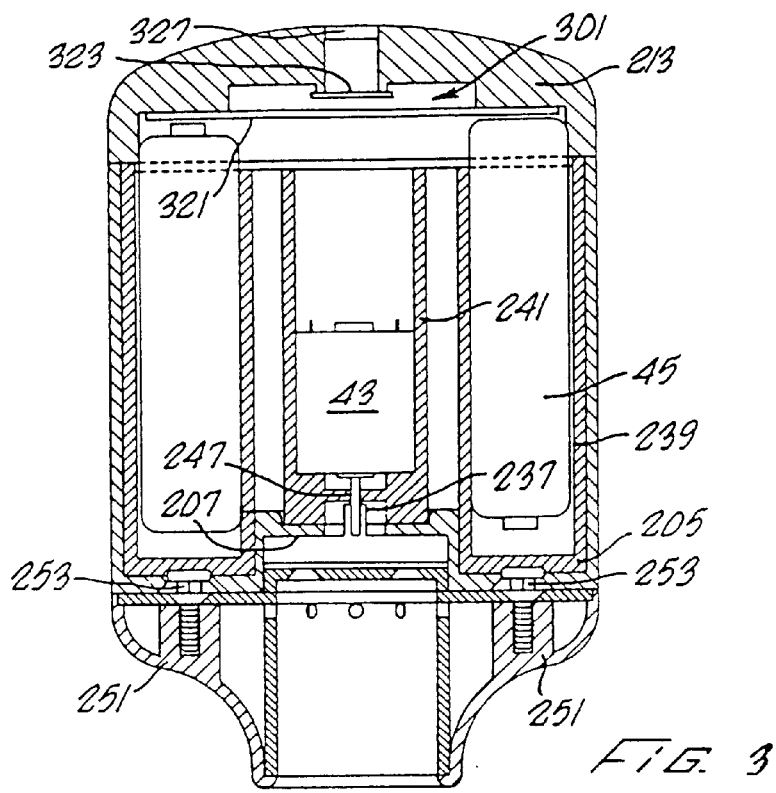
FIG. 3
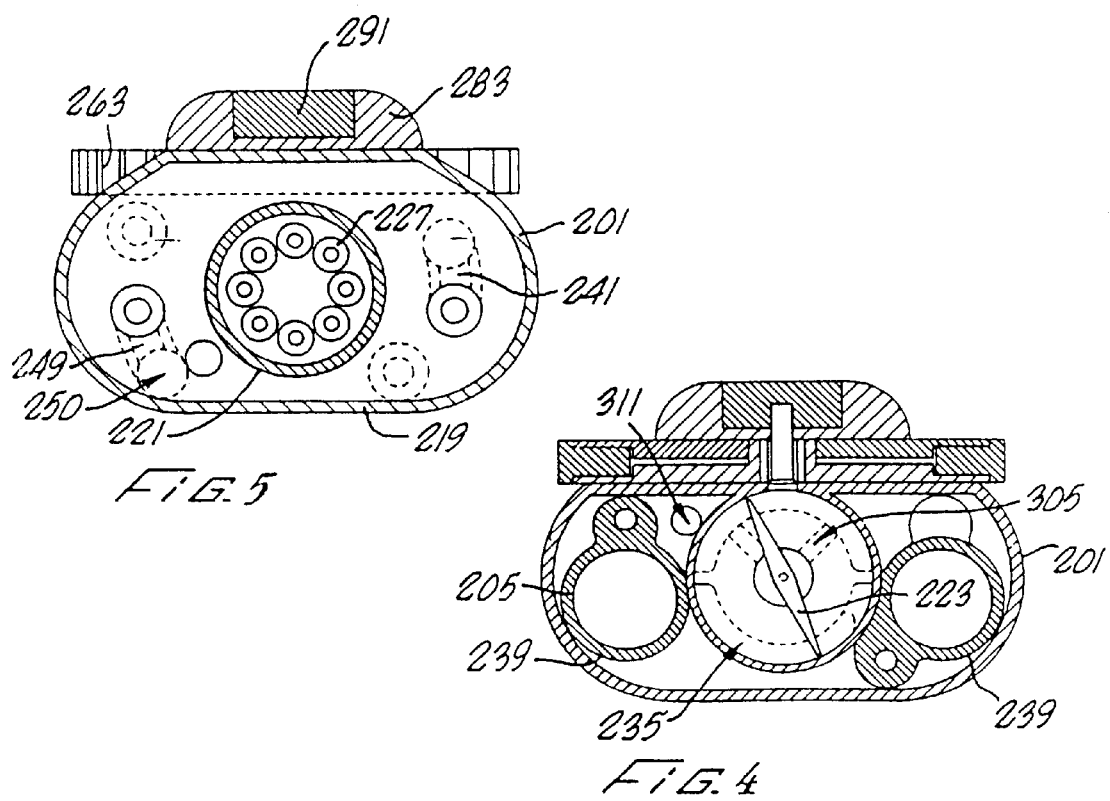
FIG. 5
FIG. 4

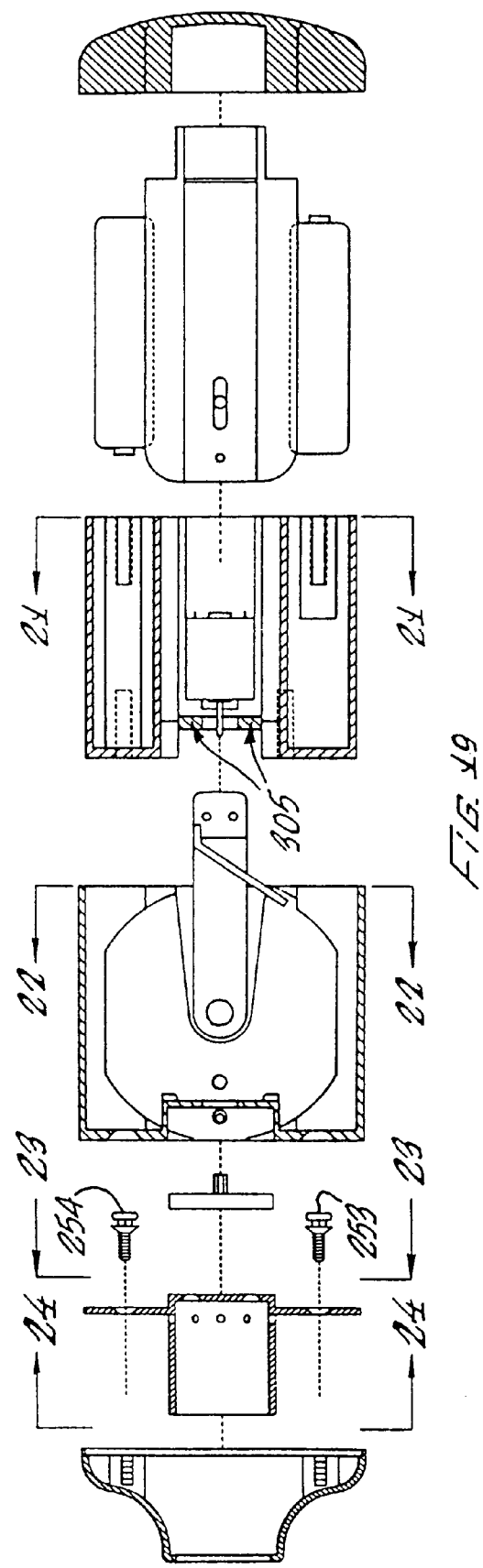

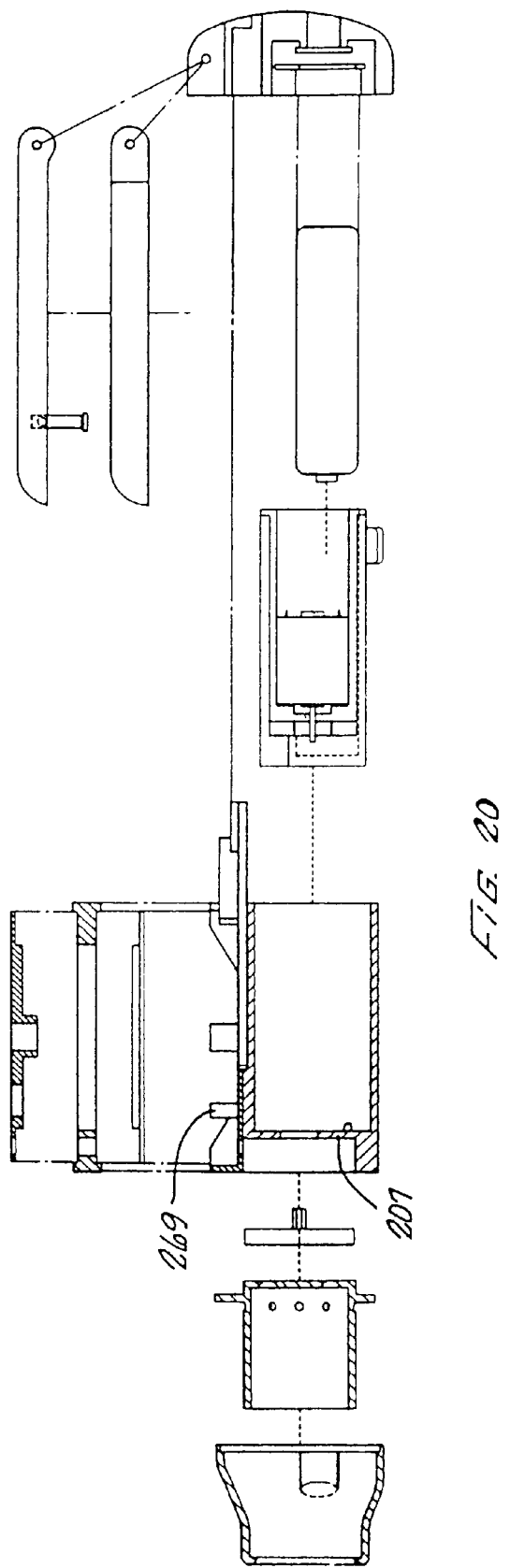

METHODS OF DRY POWDER INHALATION

This application is a continuation-in-part of Provisional U.S. patent application Ser. No. 60/016,428 filed Apr. 29, 1996.

STATE-OF-THE-ART

Considerable information regarding the in-vitro and in viv-performance of metered dose inhalers and dry powder inhalers has been reported in literature. In general, metered dose inhalers are inhalation flow rate independent, but require significant coordination and even then will deliver only about 20% of the nominal does to the lungs. Radiolabelled deposition studies of metered dose inhalers typically demonstrate the usual 3 micron particles deposit mainly in the more central airways. Recently, 3M Corporation, Minneapolis, Minn. USA, has presented data that indicates that if the particle size could be reduced to a mass median aerodynamic diameter (MMAD) of 1.5 microns an increase in the total amount of particles and peripheral deposition could result. This result appears to confirm the more uniform belief that smaller particles are required to maximize peripheral deposition (i.e. particles in the 1–2 microns size range)

Now in the case of dry powder inhalers, most studies have shown the major issue surrounding dry powder delivery is related to the flow rate dependence. The performance of the dry powder inhalers now in use vary significantly with inhalation flow rates ranging from 15 to 120 liters/min inspiratory effort. In general, at least 60 liters/min inspiratory flow has been required to consistently deaggregate a dry powder sufficiently to result in particles which could be inhaled. For some products, inhalation flow rates significantly greater than 60 L/min are required before sufficient deaggregation can occur. Both the total amount of drug formulation delivered to the patient as well as the aerodynamic particle size are affected by increasing the inhalation flow rate. For example, at 30 L/min, aerodynamic sizes of the active particles may be as large as 8 to 10 microns but above 60 L/min the same metered dose inhaler formulation may be 2–4 microns. In addition, the dose-to-dose variation may be significantly greater as the flow rate is decreased.

Unfortunately, requiring the patient to breathe forcefully when using a metered dose inhaler is in direct opposition to maximizing deposition. Traditional thinking is that 30 L/min is a well controlled inhalation flow rate. And, currently no data has been presented which shows that using existing metered dose inhaler technology, significant uniform and peripheral particle deposition had occurred, at any flow rate.

Finally, it is now generally believed that for a protein to be efficiently delivered systemically through the lungs, a very small particle size is required to facilitate peripheral deposition, preferably in the alveoli. The size often considered necessary for this purpose is in the range of one micron.

BRIEF DESCRIPTION OF THE DRAWINGS

In the drawings, wherein the same reference number denotes the same element, in all of the views:

FIG. 1 is a top plan view of the inhaler referred to below;

FIG. 2 is a section view taken along line 2—2 of FIG. 1;

FIG. 3 is a section view taken along line 3—3 of FIG. 1;

FIG. 4 is a section view taken along line 4—4 of FIG. 1;

FIG. 5 is a section view taken along line 5—5 of FIG. 1;

FIG. 6 is a front end view of the inhaler shown in FIG. 1;

FIG. 7 is a rear end view of the inhaler shown in FIG. 1;

FIG. 8 is an enlarged front elevation view of the impeller of the inhaler of FIG. 1;

FIG. 9 is a section view taken along line 9—9 of FIG. 8;

FIG. 10 is a top plan view of a drug storage device embodiment, in this case a dose cartridge, for use with the inhaler of FIG. 1;

FIG. 11 is a section view taken along line 11—11 of FIG. 10;

FIG. 12 is a top plan view of the ring portion of the cartridge of FIG. 10 showing the apertures for holding doses of dry powder;

FIG. 13 is a top plan view of the cartridge assembly of FIG. 10 including a top cover plate;

FIG. 14 is a side elevation view of the ring portion of FIG. 12;

FIG. 15 is a top plan view of the inhaler of FIG. 1 with the hold down lever flipped up or removed and the cover plates on the cartridge removed, for illustration purposes only;

FIG. 16 is a side elevation view of the inhaler of FIG. 1 showing movement of the hold down lever;

FIG. 17 is a side elevation view, in part section, of the inhaler of FIG. 1 schematically illustrating air flow paths therethrough;

FIG. 18 is a top elevation view thereof;

FIG. 19 is a top elevation exploded view of the inhaler of FIG. 1;

FIG. 20 is a side elevation view thereof, in part section;

FIG. 21 is an end view of the motor chassis, taken along line 21—21 of FIG. 19;

FIG. 22 is an end view of the housing taken along line 22—22 of FIG. 19;

FIG. 23 is a rear end view of the front cylinder taken along line 23—23 of FIG. 19;

FIG. 24 is a front end view thereof taken along line 24—24 of FIG. 19; and FIG. 25 is a graph of flow resistance of the inhaler shown in FIG. 1.

STATEMENT OF THE INVENTION

Utilizing the dry powder inhalation system described in PCT/US93/09751, published Apr. 28, 1994, and incorporated by reference (referred to here as the SPIROS system), the following in vitro and in vivo observations have been made:

1. The in vitro delivery of several drug/lactose blends has been shown to be flow rate independent over a range flow rates from 15 to 60 L/min. Both the size of the active particles and the amount of drug delivered were independent of flow rate.
2. Utilizing a radiolabelled technique, the flow rate independence of the delivery system was confirmed in vivo (15 to 60 L/min). In addition, this study clearly indicated that even with a slow inhalation rate (less than 60 L/min), the drug was delivered uniformly throughout the lung, including the periphery. In fact, there is a tendency to have higher peripheral lung deposition at the low flow rate.
3. In the metered does inhaler studies, where the in vitro determined MMAD is between 2 to 3 microns, in vivo deposition is typically quoted as between 10 to 20% of the nominal dose. Deposition of albuterol from the Spiros system was shown to be equal to or better than what is expected from metered dose inhalers, even though the aerodynamic particle size of the active particle was approximately 4.5 microns.

4. Recent pharmacokinetic (blood level) data from a comparison of beclomethasone delivered from a metered dose inhaler compared to Spiros, indicated that twice as much drug was delivered to the lung from the Spiros system. Again, the particle size of the active particle in the dry powder inhaler system was between 4 to 5 microns, while the metered dose inhaler formulation was between 3 to 4 microns.

5. Using calcitonin as a model peptide for systemic delivery, the bioactivity following dosing with the Spiros system has been estimated to be greater than 20% compared to a subcutaneous injection. In contrast, an approved nasal product has only 3% bioavailability. Surprisingly, the particle size of the calcitonin from the calcitonin/lactose blend was 4–5 microns, yet excellent systemic availability was achieved (>20%).

Using the above observations, the following conclusions regarding dry powder delivery can now be made.

Until a dry powder inhaler was developed which adequately deaggregated the powder at low inspiratory flow rates, it was not possible to separate out the performance of the dry powder inhaler from the patient inhalation maneuver. Thus, the relationship between particle size and deposition was confused with the performance of the dry powder inhaler itself. With the development of the Spiros system, we have now demonstrated that under low flow rate conditions, particle sizes which would be considered on the upper end of achieving good lung deposition can actually provide deposition uniformly throughout the respiratory tract.

Importantly, the delivery of the dry powder from the Spiros system is no longer degraded by the patient's inhalation flow rate, as is the case with existing dry powder inhalers. Slow deep inspiration is key to the increased drug delivery and peripheral deposition. Thus, the delivery system must efficiently operate under these conditions. With the deagglomerating dry powder at low inhalation flow, surprising good results were obtained over what could be expected for commercially available metered dose inhalers or dry powder inhalers.

The results which were obtained in vivo were possible because 1) Spiros is inhalation flow rate independent, and 2) Spiros efficiently deaggregates the powder. Therefore, patients were able to be trained and benefit from the slow deep inhalation maneuver. The slow deep inhalation permits more of the particles to navigate past the throat (and not be collected by impaction) and be available to deposit in the lung. Secondly, the slow deep inhalation maneuver fully dilates the lungs, driving the particles further into the lung, and inhibits premature impaction of the larger particles in the upper airways.

To facilitate the slow inhalation, some device resistance is required. If no resistance is encountered, then it is difficult for a patient to inhale slowly. This is what is often observed for metered dose inhalers and some dry powder inhalers such as Rotohaler and Spinhaler. If flow resistance is too high, patient discomfort results when the inhaler is used at the optional flow rate. It can also result in higher air velocity in passageways. This increase in velocity increases upper airway deposition by impaction. Less deposited drug is then available to the lower regions of the lung. The drug may be a systemic or topical drug for treating asthma. The drug may be a protein, a polypeptide or a hormone, for treating lung or other conditions.

DETAILED DESCRIPTION

1. A dry powder inhalation system consisting of micronized drug in the 1 to 7 micron range, alone or in blends of lactose or some other suitable inert carrier (i.e., sugars, salts).

2. The inhalation system should be flow rate independent over the range of interest, i.e., 10 or 15–60 L/min.

3. The mass median aerodynamic diameter (MMAD) of the delivered aerosol (Cascade impactor 26.3 L/min, UPS throat) should be 3.5–7 and preferably 3–6 microns. Additionally, the respirable fraction (fraction of particles penetrating the impactor inlet with a particle size less than 5.8 microns) should be greater than 20%. The most preferred level would be greater than 30 to 40%. This describes the efficiency of the device to deagglomerate the powder. A device such as the Beclomethasone Rotohaler which could be considered flow rate independent over this range delivers an aerosol of 10 microns and a respirable fraction of 2.6%.

The device resistance (slope of the flow vs. pressure drop curve (in units of (cm $H_2O^{1/2}$)) should be 0.12 to 0.21 with a most preferred range of 0.12 to 0.18.

Figure 1:
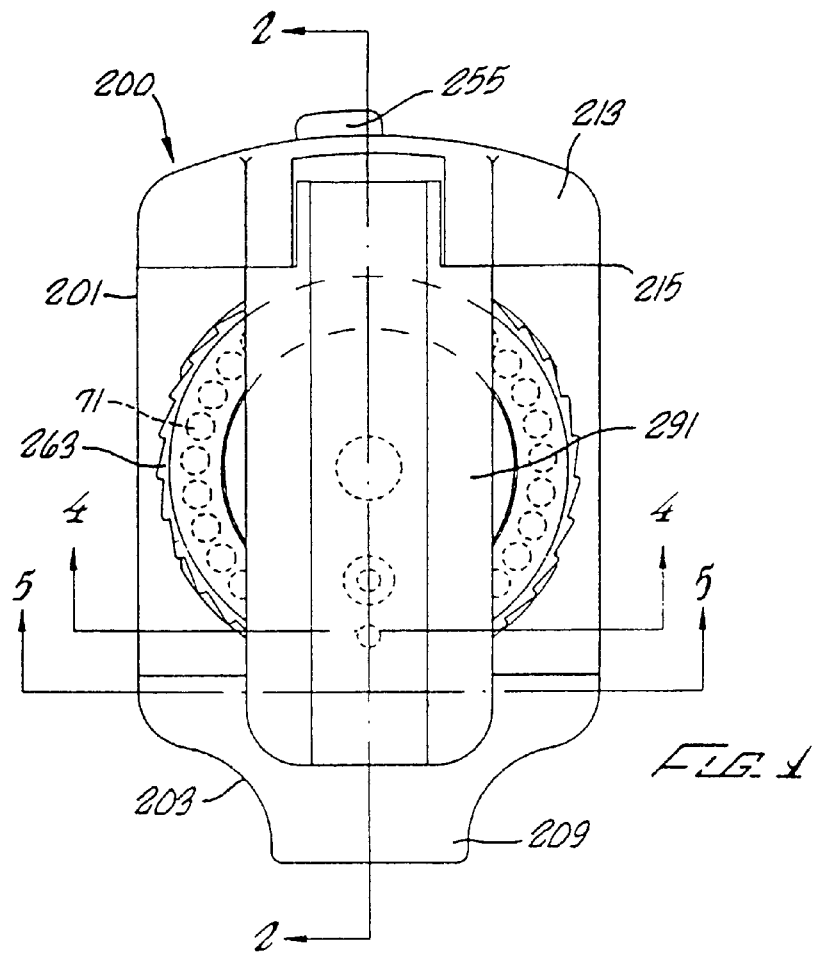
Figure 2:
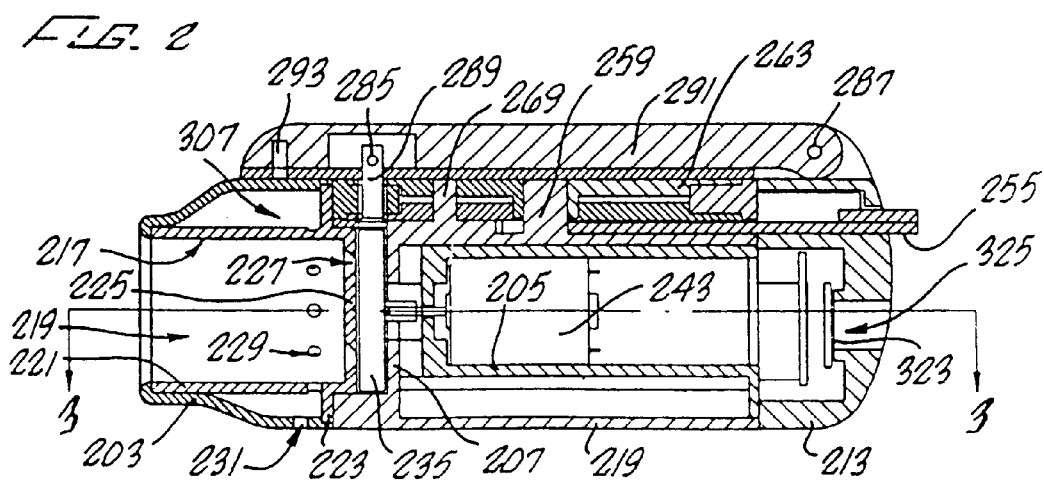
Figure 6:
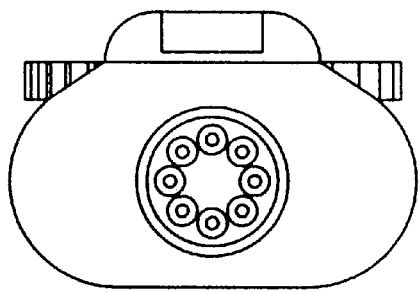
Figure 7:
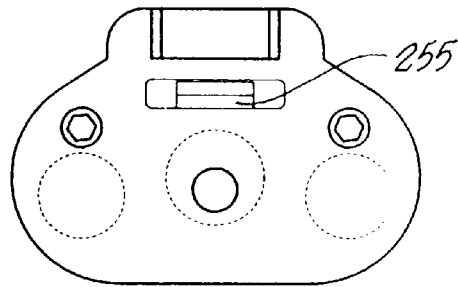

Referring to FIGS. 1 and 2, an inhaler 200 has a core or housing 201. A front end piece 203 at the front of the housing 201 tapers to a mouthpiece 209 having a diameter comfortably accommodated by the user's mouth. The housing 201 has a flat bottom surface 211. A back end piece 213 is attached to the rear of the housing 201. A powdered medicine cartridge 263 is pivotally supported on top of the housing 201, with a hold down lever 291 overlying the cartridge 263.

Figure 24:
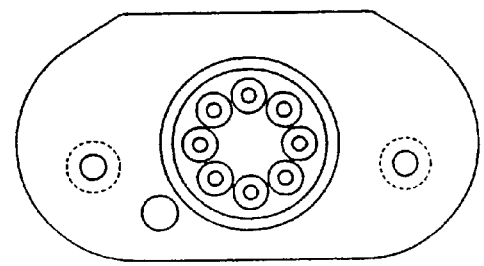
Figure 25:
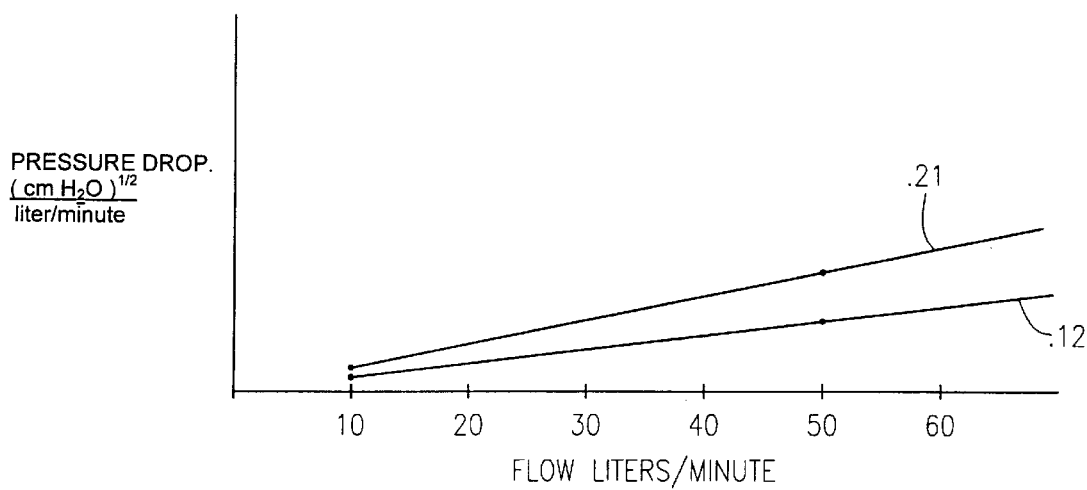

Referring to FIG. 2, a front cylinder 217 has cylindrical walls 221 and a back plate 225 which form a front chamber 219. A flange 223 extends radially outwardly from the cylindrical walls 221 just forward of the back plate 225. Countersunk outflow holes 227 pass through the back plate 225 with a feather edge or sharp edge at the rear surface of the back plate. The outflow holes 227 are preferably provided in the pattern shown in FIG. 24. Radial holes 229 extend through the cylindrical walls 221 of the front cylinder 217 into the front chamber 219 just forward of the outflow holes 227. Preferably, the radial holes 229 are provided equally spaced apart on the cylinder walls 221. A powder chute 261 extends through the top surface of the housing 201 into the impeller chamber 235. A front air inlet 231 extends through the front end piece 203 into a distribution chamber 307 formed in between the front end piece 203 and the front cylinder 217.

Figure 21:
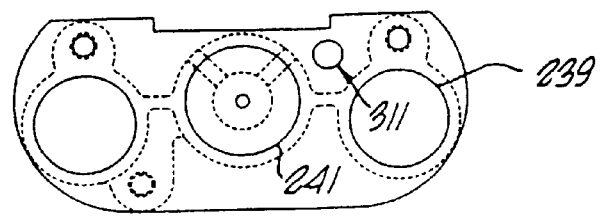
Figure 22:
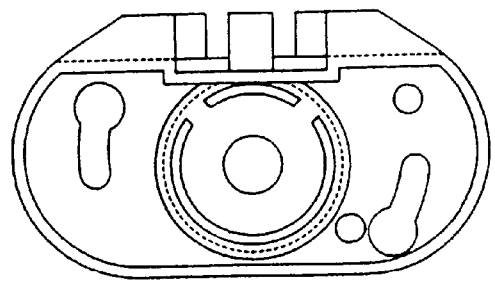
Figure 23:
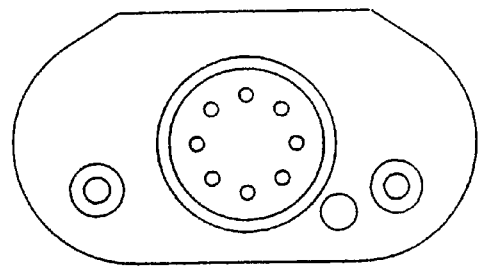

Referring to FIGS. 2, 3 and 4, a motor chassis 205 is secured within the housing 201. The motor chassis 205 has two side battery tubes 239 linked to a central motor tube 241 by webs 245, as shown in FIGS. 19–21. A partition wall 309 having an air supply hole 311 extends across the back end of the motor chassis 205.

Figure 8:
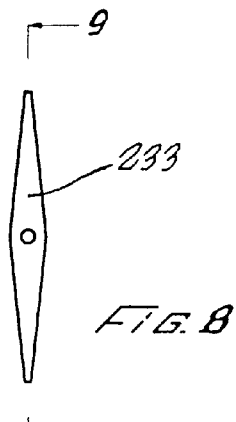
Figure 9:
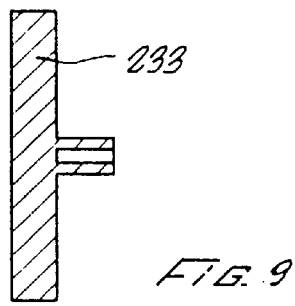

A high speed miniature electric motor 243 is contained within the forward end of the motor tube 241, as shown in FIG. 3. A motor shaft 237 extends from the motor 243 through a shaft opening in the front wall 247 of the motor tube 241, and into an impeller chamber 235. An impeller 233 is attached to the motor shaft 237 for rotation within the impeller chamber 235. As shown in FIGS. 8 and 9, the impeller 233 has two oppositely extending tapering arms forming an equilateral parallelogram.

The impeller chamber 235 is formed by a front wall 207 of the housing 201, a front rim 208 of the housing around the front wall 207, and by the back plate 225 of the front cylinder 217, although other configurations are available. The impeller chamber 235, as shown in FIGS. 2 and 3, is generally a disk-shaped open space. The impeller 233 fits within the impeller chamber 235 with a minimum clearance (preferably about 0.2–0.3mm) both front to back, i.e., between the back plate 225 and the front wall 207 of the housing, and also radially with the length or diameter of the impeller 233 only slightly less than the diameter of the rim 208. This relatively close fit of the impeller within the chamber provides proper mixing interaction of the air and powdered drug. In contrast to the first embodiment, the impeller 233 is centered in the chamber 235.

Referring to FIGS. 3 and 19, the front end piece 203 has threaded bosses 251 on either side of the mouthpiece 209. The front cylinder 217 is attached to the front end piece 203 by screws 253 extending through holes in the flange 223 and threading into the bosses 251. The screws 253 have shoulder caps 254 which extend into mounting slots 249 in the housing 201, as shown in FIG. 5. The front end piece 203 and the front cylinder 217 can be attached to the housing 201 by inserting the shoulder caps 254 through slot holes 250 in the slots 249 and rotating the front end piece 203 through an acute angle. With the reverse sequence, these pieces can be removed to access the impeller chamber 235.

Figure 13:
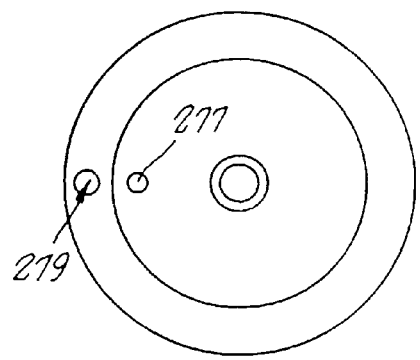
Figure 12:
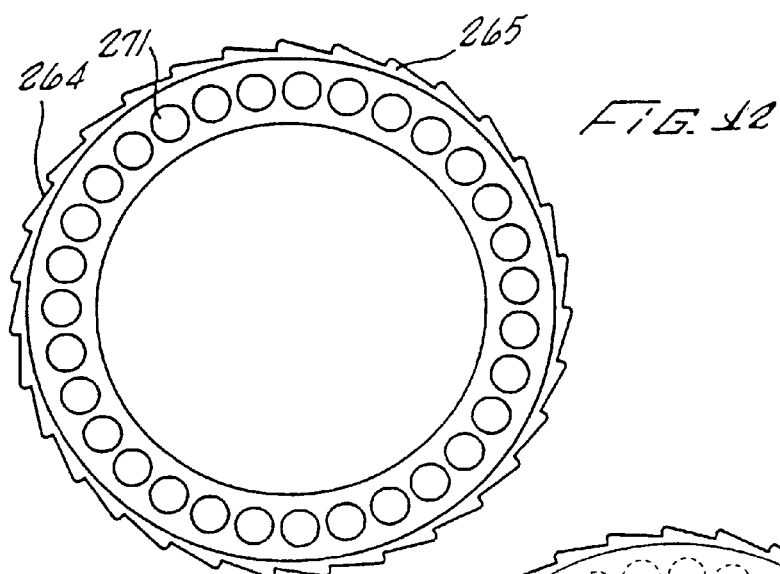
Figure 10:
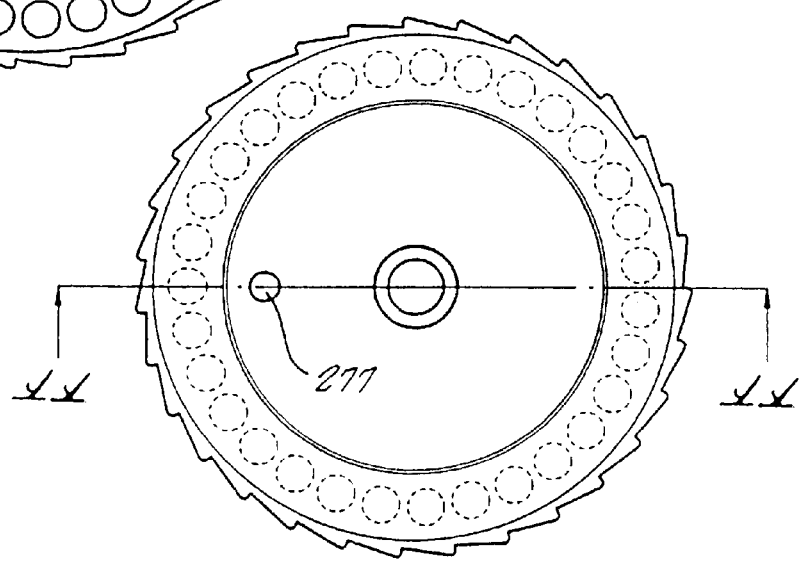
Figure 14:
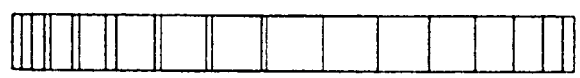
Figure 11:
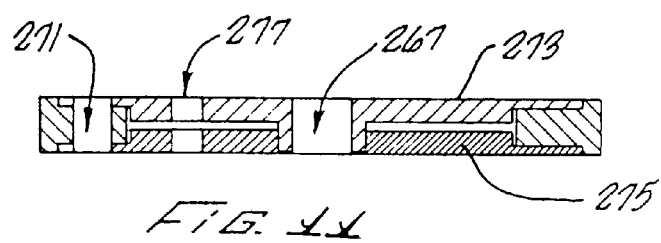

The cartridge 263 supported on top of the housing 201 includes a cartridge ring 264 having sawtooth ridges 265, as shown in FIG. 12. Holes or apertures 271 extending longitudinally through the cartridge ring 264 are loaded (e.g., at factory or pharmacy) with dry powder medication. A top plate 273 and a bottom plate 275 are attached over and under the cartridge ring 264, to form the complete cartridge 263 and to prevent leakage or contamination of the powder in the apertures 271, as shown in FIGS. 10, 11 and 13. A rivet or other fastener or joint secures the top and bottom plate over the cartridge ring 264. Anti-rotation alignment holes 277 extend through the top and bottom plates 273 and 275. A chute hole 279 in the top plate 273 and bottom plate 275 is provided so that the apertures 271 can be accessed when brought into alignment with the chute 279.

Figure 15:
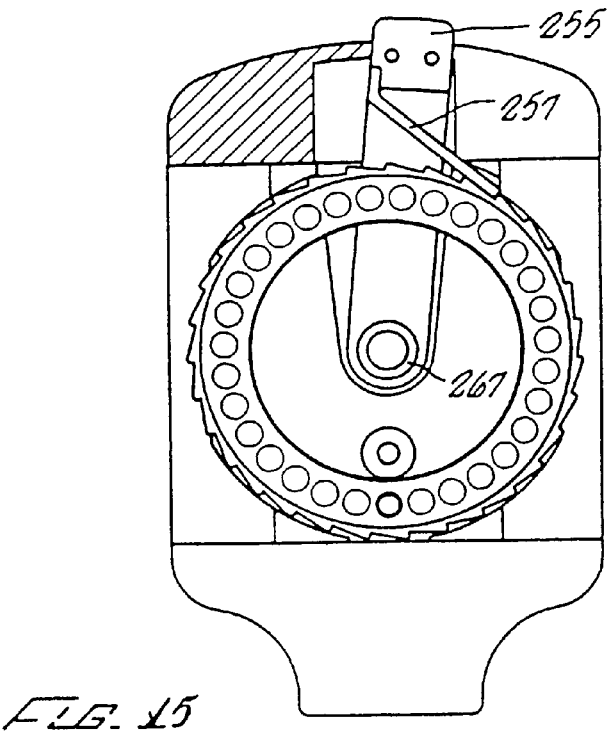

As shown in FIGS. 1, 2, 15 and 16, the cartridge 263 is placed on the housing 201 with a spindle 259 extending upwardly from the housing into the center hole 267 of the cartridge 263. A peg 269 also extending upwardly from the housing 201 passes through the peg holes 277 in the top plate 273 and bottom plate 275, to prevent the plates from turning with the cartridge ring 264. Referring to FIG. 15, a ratchet spring 257 on a ratchet support 255 on the housing 201 engages the ridges 265 around the perimeter edge of the cartridge ring 264, such that the cartridge ring can only be turned in one direction (i.e., clockwise as viewed in FIG. 15).

A lever frame 283 is pivotally attached to the back end piece 213 by a pivot pin 287. A snap 293 releasably secures the front of the lever frame 283 to the front end piece. A hold down lever 291 which nests within the lever frame 283 is also pivotally supported on pin 287. A piston 289 is pivotally attached to the hold down lever 291 by a pin 285. The piston 289 is aligned with the powder chute 261.

Figure 17:
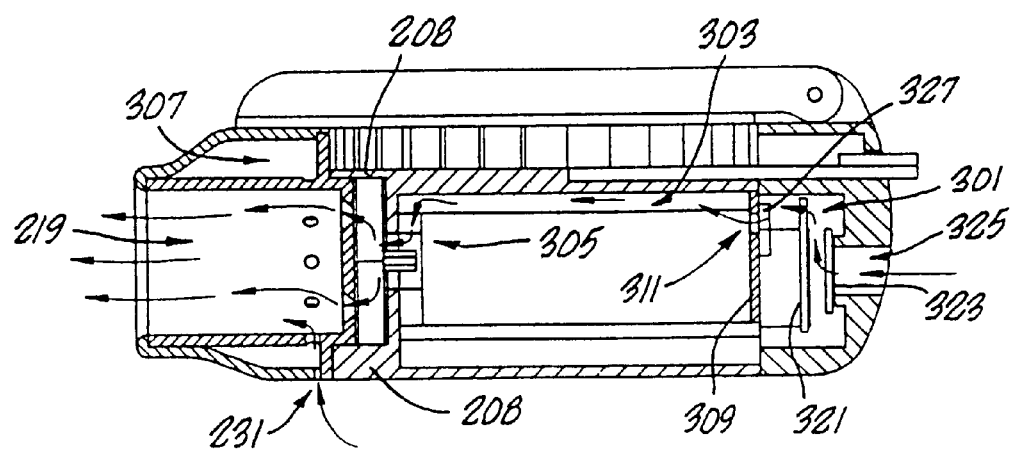

Referring to FIGS. 17 and 18, an inflow port 325 extends through the back end piece 213. A one way valve 323 separates the inflow port 325 from a rear plenum 308 in the back end piece 213. An interconnect circuit board 321 extends across the rear end piece 213. The rear plenum 301 opens into a center plenum 303 through the air supply hole 311 extending through the partition wall 309. The center plenum 303 leads forward within the housing 201 to two channel slots 305 on the front wall 207 which lead into the impeller chamber 235. A switch 329 on the one way valve 323 is electrically linked to the motor 43 and batteries 45 through the circuit board 321 to switch the motor on when the one way valve opens.

Figure 16:
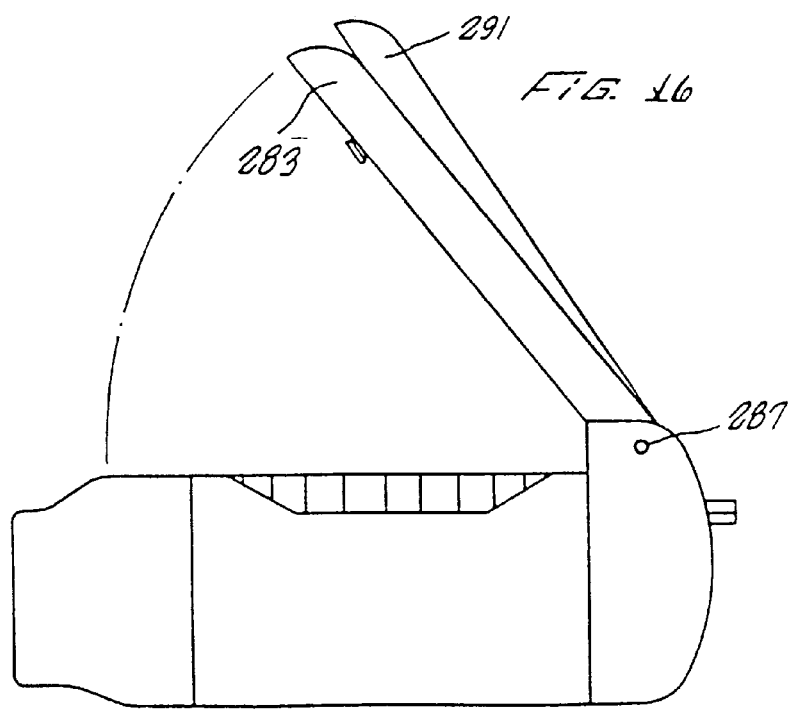
Figure 16:
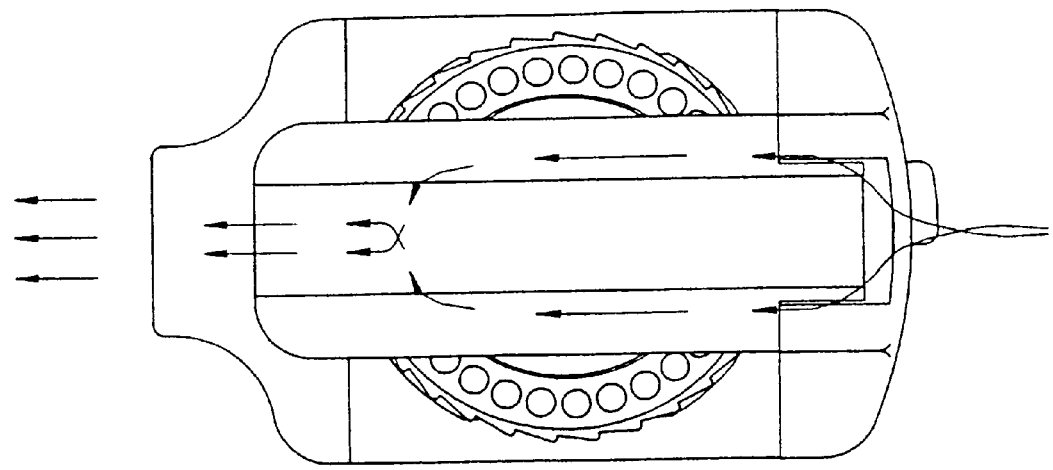

In use, a cartridge 263 is loaded onto the inhaler 200 by pivoting the lever frame 283 and hold down lever 291 upwardly, as shown in FIG. 16. The cartridge 263 is installed on the spindle 259 with the peg 269 passing through the peg holes 277 in the top and bottom plates of the cartridge 263. The lever frame 283 is pivoted back onto the housing 201, and the hold down lever 291 is pivoted down with the piston 289 aligned with an aperture 271 in the cartridge 263. As the hold down lever 291 is pressed down, the piston 289 pushes the powder medication out of the aperture 271, through the chute 261 and into the impeller chamber 235. The piston 289 is dimensioned to closely match the diameter of the apertures 271, to drive virtually all powder out of the aperture. The piston 289 also extends fully through the chute 261, so that the full dose from the aperture is pushed entirely into the impeller chamber, with virtually no powder remaining in the chute 261. The volume of the dosage is very small compared to the volume of the impeller chamber, as shown in the drawings. The inhaler 200 is then ready for use.

The mouthpiece 209 is placed into the user's mouth. As the user gently inhales, a slight pressure drop is created in the front chamber 219, and correspondingly in the impeller chamber 235, the center plenum 303 and the rear plenum 301, which are all connected. The reduced pressure in the rear plenum 301 causes the one way valve 323 to open, closing the switch 329, and energizing the motor 243. As the motor turns and spins the impeller 233 within the impeller chamber 235 (which is now loaded with a dose of medicine powder), air flows into the inhaler 200 from the inflow port 325 through the rear plenum 301, forward through air supply hole 311 into the center plenum 303, through the channels 305 and into the impeller chamber 235, as schematically illustrated in FIGS. 17 and 18. The airflow also prevents powder from flowing into the motor.

The impeller spinning at approximately 14,000 rpm efficiently mixes the powder with the air flowing through the impeller chamber. Referring still to FIGS. 17 and 18, powder-laden air passes out of the impeller chamber 235 through the outflow holes 227 and into the front chamber 219. The sharp edges on the outflow holes 227 facing the impeller chamber substantially prevent a buildup of powder in the holes, to prevent clogging. Outside air enters into the distribution chamber 307 through the front air inlet 231 which may be adjustable or varied in size to increase or decrease air flow for enhanced delivery efficiency. From the distribution chamber 307, the outside air passes radially inwardly through radial holes 229 which restrict flow by design. The outside air is intended to provide a boundary layer for the powder-laden air in the front chamber 219. The powder-laden air surrounded by the boundary layer of outside air is drawn out of the front chamber 219 into the user's mouth, throat and lungs, to deliver the powdered drug. The boundary layer helps to keep powdered drug from accumulating or collecting on the inside walls of the mouthpiece and is also believed to help to prevent the powder from settling out in the users mouth and throat. When the user stops inhaling, the valve 323 closes opening the switch 329 and stopping the motor. The inhaler accordingly is breadth actuated. Since the valve 323 opens with even a slight pressure drop, the inhaler requires only slight inhalation to turn on.

The inhaler 200 produces a slow moving aerosol mist of fine powder that can be easily and safely inhaled deep into the lungs to maximize the actual delivered dosage and effect of the drug. Unlike many prior inhalers, the present inhaler does not require excessive or deep inhalation to achieve drug delivery. Accordingly, the user's lung function is not nearly so important as in the prior art. The present inhaler is therefore highly advantageous for use by persons with impaired lung function.

In addition, exhalation into the inhaler 200 is prevented as the one way valve 323 closes with only a slight pressure rise in the rear plenum 301. If the user coughs or blows into the inhaler 200, some of the moisture laden breath will exhaust out in part through the front air inlet 231 but will not appreciably reach into the impeller chamber, absent repeated or excessive exhalation into the inhaler.

The present inhaler may include design features provided by the recognition that different powdered drugs have different characteristics. Powdered mixtures of drugs have varying particle sizes and distributions, densities, cohesiveness (the tendency for the drug particles to stick to themselves) and adhesiveness (the tendency for the drug particles to stick to surfaces of the inhaler). Thus, for increased delivery efficiency, the flow parameters of the inhaler should advantageously be adjusted for the specific drug being delivered. These adjustments can be made by adjusting the rotation speed of the impeller 233, and by varying the air flow through the impeller chamber. The air flow through the impeller chamber can be controlled by a slide or dial aperture 327 increasing or decreasing the size of the opening of the air supply hole 311. Alternatively the air supply hole 311 can be punched or drilled out to a specific size dedicated to a specific drug. Consequently, the inhaler is advantageously provided with speed setting or adjusting circuitry for the motor and an air flow control aperture or air supply hole size matched to the characteristics of the drug that the inhaler will deliver.

Electrical wiring in these drawings has not been shown for clarity as such wiring is already known in the prior art. The drawings show the preferred sizes of the features of the inhaler.

While the invention has been described with reference to particular embodiments, those skilled in the art will be able to make various modifications to the described embodiments without departing from the spirit and scope thereof.

We claim:

1. A method for inhalation of a dry powder drug, comprising the steps of:
    a) providing a dry powder drug composition having a drug particle size of from about 1–7 microns and mass median aerodynamic diameter of the delivered aerosol of from about 3 to 6 microns;
    b) loading the dry powder drug composition into an inhaler which is generally flow rate independent, and with the inhaler having an inspiration flow resistance of about 0.12 to 0.21 (cm H$_2$O)$^{1/2}$) over the range of about 10–60 L/min;
    c) inhaling the drug composition from the inhaler with an inspiration flow rate of about 15–60 L/min, resulting in a delivery efficiency measured by respirable fraction of at least 20%.

2. The method of claim 1 wherein the drug composition includes active particles and the aerodynamic particle size of the active particles is about 4.5 microns.

3. The method of claim 1 wherein the drug comprises a systemic or a topical drug for treating asthma.

4. The method of claim 1 wherein the drug comprises a protein, a polypeptide, or a hormone.

5. The method of claim 1 wherein the percent of particles greater than 5 microns is about 30–90.

6. The method of claim 1 wherein the inhaler has a flow resistance of from about 0.12 to 0.18 (cm H$_2$O)$^{1/2}$.

7. The method of claim 1 wherein the drug composition includes an inert carrier.

8. The method of claim 1 wherein the drug comprises beclomethasone.

9. The method of claim 1 wherein the respirable fraction (fraction of particles penetrating the impactor inlet with a particle size less than about 5.8 microns) is at least 20%.

10. The method of claim 1 wherein the flow resistance is about 0.12 to 0.21 (cmH$_2$O)$^{1/2}$ over the range of 15–60 L/min.

11. The method of claim 1 wherein the mass median aerodynamic diameter of the delivered aerosol is from about 3.5 to 5.5 microns.

12. A method for inhalation of a dry powder drug, comprising the steps of:
    a) providing a dry powder drug composition having a drug particle size of from about 1–7 microns and mass median aerodynamic diameter of the delivered aerosol of from about 3 to 6 microns;
    b) loading the dry powder drug composition into an inhaler which is generally flow rate independent, and with the inhaler having an inspiration flow resistance of about 0.12 to 0.21 (cm H$_2$O)$^{1/2}$) over the range of about 10–60 L/min;
    c) inhaling the drug composition from the inhaler with an inspiration flow rate of about 15–60 L/min, resulting in a delivery efficiency measured by respirable fraction of at least 20%.

* * * * *